United States Patent [19]

Cox

[11] Patent Number: 4,511,552
[45] Date of Patent: Apr. 16, 1985

[54] DEODORANT-DISPENSING PRODUCTS AND DISPENSING PROCESS

[76] Inventor: James P. Cox, 246 E. Bartlett Rd., Lynden, Wash. 98264

[21] Appl. No.: 508,172

[22] Filed: Sep. 23, 1974

[51] Int. Cl.$^3$ ............................................. A61L 9/01
[52] U.S. Cl. ........................................ 424/14; 239/60; 424/16; 424/19; 424/76; 424/93; 424/94; 424/DIG. 10
[58] Field of Search ...................... 424/76, 65, 14, 16, 424/19, 93, 94, DIG. 10; 210/2, 11

[56] References Cited

U.S. PATENT DOCUMENTS

| | | | |
|---|---|---|---|
| 2,691,615 | 10/1954 | Turner et al. | 424/76 |
| 2,865,806 | 12/1958 | Bulloff | 424/76 |
| 2,927,055 | 3/1960 | Lanzet | 424/76 |
| 3,097,129 | 7/1963 | Laffetay et al. | 424/76 |
| 3,098,703 | 7/1963 | Snyder et al. | 424/76 |
| 3,236,726 | 2/1966 | Ross . | |
| 3,375,159 | 3/1968 | Batton | 424/76 |
| 3,446,893 | 5/1969 | Hanford | 424/76 |
| 3,767,787 | 10/1973 | Segal | 424/76 |
| 3,775,448 | 11/1973 | Guhr et al. | 424/65 |
| 3,943,243 | 3/1976 | Kook | 424/76 |

OTHER PUBLICATIONS

Shepard-The Chemistry and Action of Insecticides (1951), pp. 115, 179 and 180.
The Merck Index-ninth edition (1976), p. 2925.
Copley-Chem. Abst., vol. 63, (1965), p. 17796a.
Silvey-Chem. Abst., vol. 68, (1968), p. 107,827f.
Chem. Abst.-8th Collective Index, vol. 66-75, 1967-1971, p. 5637s.

*Primary Examiner*—Allen J. Robinson
*Attorney, Agent, or Firm*—Robert W. Beach

[57] ABSTRACT

Deodorant-dispensing products include volatile solid deodorant, release retardant which will cause the deodorant to vaporize slowly over an extended period of time, a binder and/or carrier or flotation agent such as paraffin or gelatin, and perhaps other ingredients such as sawdust or clay as absorbent and biodegradant material. The product may take various forms. One form is an extrudable gel which will adhere to a surface and will solidify quickly on exposure to air. Such gel can also be used as a vehicle for insecticides or insect repellents. Another product is a solid, useful for deodorizing heated malodorous organic material such as animal, fish or poultry waste which is being rendered. A further solid product for deodorizing liquid and/or fumes emitted from such liquid is floatable and can have an adjunct incorporating biodegradant for biodegrading material of the liquid. The floater can include two components, one in the form of an annulus and the second, a core received in the aperture of the annulus and carried by it. Suitable deodorants are musk xylene, vanillin, lemon oil or limonene, and 2,3 butanedione. Suitable release retardants are paradichlorobenzene, paranitrochlorobenzene, dinitrobenzene, dinitrotoluene, dinitronaphthalene, dichloronitrobenzene, dinitrochlorobenzene, and benzophenone. Biodegradants include bacterial cultures, fungi and enzymes. Nutrients for such material may also be provided.

35 Claims, 1 Drawing Figure

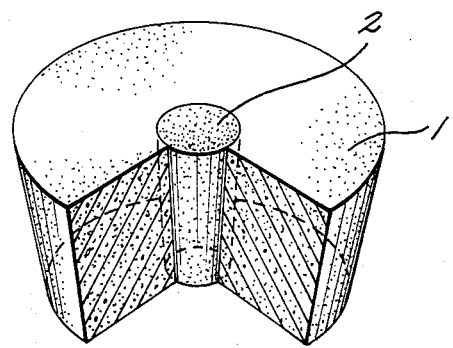

DEODORANT-DISPENSING PRODUCTS AND DISPENSING PROCESS

This invention relates both to deodorant products of special character and to the method for using such special products.

A principal object of the invention is to provide special deodorant products having unique capabilities, and which are effective for neutralizing or masking a variety of molodors over an extended period of time. A further object is to provide such deodorant products which are substantially completely dissipated when their deodorizing capabilities have been exhausted.

More specifically it is an object to provide a gel type of product which will adhere to a surface and solidify, a solid product which can be handled readily and a solid floating product which can include both deodorant for deodorizing airborne malodors and biodegradants for treating over an extended period of time material in the liquid on which the product floats.

Another object is to provide a method of handling and placing deodorant for local deodorizing such as in rest rooms. It is also an object to provide a method for treating effectively over an extended period of time malodorous gas escaping from a sewage lagoon, and also to provide a source of biodegradant material, such as bacteria, fungi and enzymes, which will be supplied to the liquid of the lagoon over a prolonged period.

A principal purpose of the products of the present invention is to deodorize a wide variety of malodors.

In this description the word "deodorize" is used broadly to refer to chemical neutralization of malodorous substances, such as by providing an acid substance to react with a malodorous base and produce a salt having an inoffensive odor, or reodorizing by providing a substance which will react with a malodorous substance to produce a pleasant odor, or simply masking an unpleasant odor by mixing with it material having a more pronounced pleasant odor so as to overcome the effect of the objectionable odor.

Odors which the products of the present invention are capable of deodorizing are trimethylamine having a fishy odor, skatole and indole having the odor of feces and sewage, acrolein having an acrid ordor such as produced by rendering animal, poultry and fish waste, butyric acid having the odor of rancid butter, secondary and tertiary ammonia compounds, putescence having the odor of rotting vegetation, and cadaverine having the odor of decaying flesh. While the product of the present invention will not eliminate all of such malodors, such products will at least counteract or mask those odors so as to provide an aesthetically acceptable atmosphere to breathe.

The drawing is a top perspective of a floater product with parts broken away.

All of the deodorant products include deodorant such as musk xylene crystals, $C_{12}H_{15}N_3O_6$, vanillin, $CH_3O(OH)C_6H_3CHO$, lemon oil or limonene, $C_{10}H_{16}$, and 2,3 butanedione or biacetyl, $CH_3COCOCH_3$; release retardant including paradichlorobenzene, $C_6H_4Cl_2$, (See U.S. Pat. No. 1,346,337), paranitrochlorobenzene, $C_6H_4ClNO_2$, (See U.S. Pat. No. 1,515,364), dinitrobenzene, $C_6H_4(NO_2)_2$, dinitrotoluene, $C_7H_6O_4N_2$, dinitronaphthalene, $C_{10}H_6O_4N_2$, dichloronitrobenzene, $C_6H_3Cl_2NO_2$ dinitrochlorobenzene, $C_6H_3O_4N_2Cl$, benzophenone, $C_6H_5COC_6H_5$, and 2,3 butanedione solidified with phosphoric acid, $C_4H_6O_2\text{-}2H_3PO_4$; and binder and/or plasticizer such as paraffin, gelatin, agar-agar, carrageenin, pectin, cellulose derivatives such as methylcellulose, carboxymethylcellulose, hydroxypropyl methylcellulose and sodium carboxy-methylcellulose, and sorbitan derivatives and complexes such as sorbitan polyoxyethylene monooleate, sorbitan polyoxyethylene monostearate and sorbitan monostearate. The 2,3 butanedione deodorant could be used in the solid compound form of phosphoric acid and biacetyl crystals, $C_4H_6O_2.2H_3PO_4$, instead of in the liquid form. Other ingredients particularly suitable for incorporation in special products will be pointed out in connection with such products.

Gel Product

A problem of deodorizing a limited space, such as a rest room, involves providing a form of or container for deodorant which is visually unobtrusive and a deodorant which is persistently effective for a long period of time, can be located where it is most effective and is not apt to be vanadlized. When deodorant is placed in a container secured to a wall, it is considered to be unpleasantly obtrusive by many, and provides a challenge to others inviting the container to be removed or broken. Moreover, such containers can practically be placed at only one or two locations in most public rest rooms so that their effectiveness is not at all uniformly or appropriately distributed. The gel product of the present invention can be extruded from a collapsible tube or plastic bottle onto a surface whether horizontal, vertical or inverted to form a daub or ribbon of material which will solidify quickly after it is exposed to the air.

Consequently, any amount of the gel can be placed at any location and at as many locations as may be desired without reliance on any holding and/or dispensing device. A daub or daubs or a ribbon or ribbons may, for example, be applied to the underside of a toilet seat, or to the underside of or alongside a urinal. Such a daub or ribbon would not particularly challenge a person to remove it. The material can be applied quickly. Action of the material to deodorize involves the material being dissipated slowly, which automatically removes the material of the daub or ribbon. When the material has been completely spent, little or no residue remains to be cleaned off the surface.

The gel includes deodorant of one or more of the types recited above, release retardant which greatly deters and prolongs the volatilization of the deodorant component, and binder and/or plasticizer. The binder plasticizes the deodorant and the release retardant so as to form a gel that can be extruded readily. Optionally soap and ammonia can be included as deodorant absorbent carrier in the gel. A representative formula for the gel product contains the following ingredients by weight:

| | |
|---|---|
| deodorant | 0.1 to 50 percent |
| release retardant | 10 to 80 percent |
| binder and/or plasticizer | 1 to 50 percent |

A formula specifying representative ingredients by weight is:

| deodorant | |
|---|---|
| musk xylene | 0.1 to 30 percent |
| vanillin | 0.1 to 30 percent |

| -continued | |
|---|---|
| limonene release retardant | 0.1 to 35 percent |
| paradichlorobenzene binder & plasticizer | 5 to 65 percent |
| paraffin absorbent | 5 to 70 percent |
| soap | 0 to 30 percent |
| ammonia | 0 to 3 percent |

Preferred proportions of the aforesaid representative ingredients are:

| musk xylene | 15 percent |
|---|---|
| vanillin | 15 percent |
| limonene | 30 percent |
| paradichlorobenzene | 15 percent |
| paraffin (low melt) | 15 percent |
| soap | 9 percent |
| ammonia | 1 percent |
| total | 100 percent |

Ammonium hydroxide and soap are heated to 150° F. and mixed, followed by cooling to room temperature. The paraffin is melted and the various ingredients are added, the total mixture is mixed together, poured into tubes or squeezable bottles and sealed.

From a gel of this general type which has been solidified in a daub or a ribbon, deodorant will be vaporized over a long period of time, such as a week to several months, depending upon the particular composition of the gel and the size and thickness of the daub or ribbon. The volatile deodorant will be released more rapidly at higher temperatures and less rapidly at cooler temperatures. In order to release the deodorant, the release retardant must also be vaporized so that the daub or ribbon is progressively dissipated until it has virtually disappeared when all of the deodorant has been released.

Ordinarily the gel product of the present invention will not contain 2,3 butanedione, except for industrial operations, because the deodorizing capability of such substance is much greater than normally is required for deodorizing locations in which the extrudable gel would normally be used.

The gel type of carrier can be used as a carrier for insecticide instead of or in addition to serving as a vehicle for deodorant. If the gel is to be used for dispensing both deodorant and insecticide, an appropriate insecticide can simply be added to the gel formula. Suitable insecticides include 2,2-dichlorovinyl dimethyl phosphate or dichlorovos, $C_4H_7Cl_2O_4P$, which is sold under the trade name "Vapona", dieldrin, $C_{12}H_8OCl_6$, malathion, $C_{10}H_{19}O_6PS_2$, pyrethrin I, $C_{21}H_{28}O_3$, and pyrethrin II, $C_{22}H_{28}O_5$. The insecticides are effective to kill mosquitos, carpenter ants, termites and cockroaches, for example. The amount of insecticide included in a deodorant gel could be from 0 to 25 percent, a preferred proportion being approximately 4 percent. Such insecticides could also be dispensed in the gel as a carrier without the deodorants such as musk xylene, vanillin and limonene, in which instance the proportion of insecticide could be greater, such as approximately 8 percent. In addition, the gel could include with the insecticide attractants for insects such as pheromones, which include geraniol, eugenol anisyl acetone, methyl eugenol, sec-butyl 6-methyl-3-cyclohexene-1-carboxylate (siglure), anethole, 10-trans-12-cis-hexadecadien-1-OL 9-octadecene, and sec-butyl 4 (or 5) -chloro-2. The proportion of such pheromones in liquid form would be 0 to 35 percent by weight, a preferred proportion being 15 percent.

The gel could also be used as a vehicle for insect repellent, such as dinitropropylisocinchomeranate, n-propyl N,N-diethylsuccinamate benzyl benzoate, 2-phenylcyclohexanol, 2-ethylhexanediol-1,3, 2-ethyl-2-butyl-propanediol-1,3, dimethyl phthalate, and N-butylacetanilide. The proportion of such repellent could be within the range of 0 to 40 percent by weight by weight, a preferred proportion being approximately 20 to 25%.

Solid

A principal use for the initially solid product of the present invention is for deodorizing conditions in which malodors are acute, or produced in a large volume in a concentrated area. An example of such a situation is in a rendering plant for animal, poultry and/or fish products. The solid deodorant product can be supplied in formed or molded elements of block, pellet or stick form which can be placed in the material being rendered. Such rendering may be for the purpose of producing animal feed, fertilizer, lard, tallow, soap or adhesives. Because such rendering is accomplished at rather high temperatures, such as 150° F. to 250° F., the release of the volatile deodorant will be retarded much less than at lower temperatures. The deodorant acts to deodorize the gas and steam liberated from the organic material being rendered by the rendering process.

Because of the high volume of malodorous gas evolved from a large rendering cook, use of a powerful deodorant is appropriate and justified. Consequently, for such purposes as deodorizing organic rendering cooks, utilization of 2,3 butanedione is recommended. Ordinarily it is preferred that such deodorant be used in conjunction with other deodorant such as musk xylene and/or vanillin. Because the 2,3 butanedione is in the form of liquid, instead of being crystalline like musk xylene and vanillin, the binder and/or plasticizer component will provide a binding action which will enhance the firmness of the product even at higher temperatures to increase the volatilization retarding action of the release retarant.

A representative formula for the solid product of the present invention is by weight:

| 2,3 butanedione | 0.01 to 10 percent |
|---|---|
| crystalline deodorant | 1 to 30 percent |
| release retardant | 1 to 30 percent |
| binder | 1 to 50 percent |

Representative ingriedents which could be used in such a formula are by weight:

| deodorant | |
|---|---|
| 2,3 butanedione | 0.01 to 10 percent |
| musk xylene | 1 to 30 percent |
| vanillin | 1 to 30 percent |
| limonene | 0.01 to 20 percent |
| release retardant | |
| paradichlorobenzene | 1 to 30 percent |
| binder | |
| paraffin (low melt) | 3 to 50 percent |

A preferred specific formula includes the following proportions of the ingredients by weight:

| | |
|---|---|
| 2,3 butanedione | 8 percent |
| musk xylene | 15 percent |
| vanillin | 15 percent |
| limonene | 7 percent |
| paradichlorobenzene | 25 percent |
| paraffin (low melt) | 30 percent |

The solid product is made by melting the paraffin, adding the paradichlorobenzene, the musk xylene and the vanillin and mixing them together at a temperature sufficiently high to maintain the paraffin melted, such as approximately 160° F., and then mixing in the liquid 2,3 butanedione and the liquid limonene while the mixture is cooling. After the ingredients have been thoroughly mixed together, the still fluid or plastic body is poured or packed into molds to cool and set into blocks, pellets or sticks of desired size. A pellet or a stick of substantial size, such as one weighing approximately seven ounces will deodorize satisfactorily effluent gas from an organic material rendering cook of three tons of animal, fish and/or poultry waste material.

Floater

Especially near or in inhabited communities odors from a sewage lagoon, or a lagoon receiving waste from an industrial plant, produces malodors offensive to the neighborhood. Stabilization by natural processes to a point where malodor is negligible may require a period of several months. Some lagoons relying on the action of aerobic bacteria are shallow and may be agitated mechanically and/or aerated. Such lagoons are designated activated sludge lagoons.

Other lagoons are deeper and are quiescent. Such lagoons are usually used seasonally by food processors and renderers as natural sewage-settling tanks, and on farms. Especially such lagoons can create objectionable odors and problems, particularly downwind from the lagoon.

The floater of the present invention is particularly efficacious for deodorizing effluent gases from lagoons over an extended period of time. Preferably the floater attacks the odor problem in two ways: first that of deodorizing effluent gas and, second, providing biodegradant material to the lagoon, that is, material which will promote and expedite the biodegradation of organic material in the lagoon liquid. In addition, the floater can incorporate an ingredient to cover the surface of the lagoon for deterring escape of gas from it.

A representative type of durable floater is shown in the drawing in which the float component 1 is illustrated as being a form-sustaining solid of annular shape. Preferably its exterior periphery tapers downward, so as to identify top and bottom of the article. The central aperture tapers from top to bottom to receive and hold a downwardly tapered core plug 2 as an adjunct to the float 1.

A representative formula for the composition of the annulus 1 by weight is as follows:

| | |
|---|---|
| deodorant | 5 to 50 percent |
| release retardant | 5 to 35 percent |
| binder substantially nonreactive chemically with water and substantially insolubles in water | 2 to 40 percent |
| surface coating material | 5 to 65 percent |
| Buoyant material substantially nonreactive chemically with water and substantially insoluble in water | 10 to 90 percent. |

Specific ingredients for the floater could include the following by weight:

| | |
|---|---|
| deodorant | |
| musk xylene | 0 to 20 percent |
| vanillin | 0 to 20 percent |
| 2,3 butanedione | 0.01 to 15 percent |
| limonene | 0 to 15 percent |
| release retardant | |
| paradichlorobenzene | 0 to 25 percent |
| binder | |
| paraffin | 2 to 30 percent |
| surface coating | |
| cetyl alcohol $C_{16}H_{33}OH$ or mineral oil | 0.01 to 15 percent |
| buoyant material which is substantially nonsoluble in water and which is substantially nonreactive chemically with water | |
| sawdust | 10 to 90 percent |

The paraffin and sawdust, which are the principal ingredients, do not react chemically with water and are not appreciably soluble in water, provide buoyancy for the floater so that the entire specific gravity of the composite floater is less than 1. Such ingredients form a body of substantial size stably form-sustaining when floating in contact with water.

A specific suitable formula for the float component of the floater could include the following ingredients in the proportions specified by weight:

| | |
|---|---|
| musk xylene | 2 percent |
| vanillin | 8 percent |
| 2,3 butanedione | 2 percent |
| limonene | 2 percent |
| paradichlorobenzene | 8 percent |
| paraffin | 47 percent |
| cetyl alcohol $C_{16}H_{33}OH$ | 2 percent |
| sawdust | 29 percent |
| total | 100 percent |

The float component is made by heating the paraffin until it is melted, mixing with it the musk xylene, vanillin and the paradichlorobenzene. When these ingredients have been thoroughly mixed the liquid ingredient 2,3 butanedione, limonene and cetyl alcohol are mixed, added to the mixture and, finally, the sawdust is mixed in. The resulting mixture is sufficiently plastic so that it can be packed into molds to set.

The core portion 2 of the floater provides biodegradants which will assist in biodegrading carbohydrate, protein, fat, hair, polysaccharides and other material dissolved or suspended in the liquid of the lagoon. The core can supply bacteria, fugi and enzymes for this purpose. The bacteria, for example, may be *Streptococcus fecealis* and/or *Streptococcus diacelylactis*. The fungi, for example, may be yeast such as *candida pseudotropicalis* or *saccharomyces cereviseae*. The enzymes, for example, may include lipase, chitinase, proteinase and carbohydrase. The core may include sawdust, clay and/or papier-mache' serving as absorbents to provide body for the core. These materials are substantially insoluble in water and substantially nonreactive chemically with water. The clay serves as insert filler and binder. Also, it may be desirable to provide nutrients for the bacteria and fungi in the form of sugar.

A representative formula for the core 2 can include the following ingredients by weight:

| | |
|---|---|
| sawdust | 0 to 5 percent |
| clay | 5 to 80 percent |
| mixed culture of bacteria and fungi | 1 to 50 percent |
| enzymes | 0 to 50 percent |
| sugar | 0 to 50 percent |

A satisfactory formula for the core may include:

| | |
|---|---|
| sawdust, clay and/or papier-mache' | 50 percent |
| clay | 10 percent |
| mixed culture of bacteria, fungi and yeast | 35 percent |
| enzymes | 4 percent |
| sugar | 1 percent |
| total | 100 percent |

In addition, the float component 1 or the core 2 or both may include buffer material for adjusting the pH of the lagoon liquid.

Composite floaters can simply be placed at strategic locations on a lagoon, and may either be anchored or may float freely. The surface covering ingredient will be released to provide an essentially monomolecular coating on the surface of the lagoon to deter escape of the gas from the liquid. The deodorants of the float will deodorize such gas as does escape. Particularly the 2,3 butanedione is a very powerful and effective deodorant which will deodorize over a wide area. In a typical situation a single floater will deodorize gas escaping from a lagoon over an area of approximately 10,000 square feet at a temperature of 70° F. persistently throughout an extended period of time, such as approximately a month because it is in the form of a body of substantial size stably form-maintaining when floating in contact with water. Consequently, floaters should be placed on a lagoon not over 100 feet apart to be most effective. The surface coating should also cover approximately the same area. Alternatively, the floaters can simply be stationed near the prevailing downwind edge of the lagoon, or be free to be blown by wind toward such edge so that windborne gases leaving the lagoon area will be properly deodorized.

The bacteria, fungi, and enzymes of the core will be leached into the liquid of the lagoon. If the lagoon liquid contains a large amount of grease or tallow, an exceptionally large proportion of lipase should be included in the core.

The floater will be effective to deodorize the atmosphere over a lagoon throughout a temperature range of 35° F. to 105° F. and for pH values of the lagoon liquid between 5.0 and 10.8, and preferabloy within the range of 6.5 to 8.0, the optimum being approximately 7.4. The bacteria and enzymes will function effectively if the temperature of the liquid in the lagoon is between 55° F. and 98° F. Acid or alkali may be supplied by the floater to adjust the pH of the liquid to the extent necessary for effective treatment of the liquid.

The higher the temperature, the more malodorous gas will escape from the lagoon, but the retarding action of the release retardant is also reduced at higher temperatures so that more deodorant will be released from the floater to counteract the increased quantity of malodorous gas escaping.

2,3 butanedione

An important deodorant for deodorizing large volumes of concentrated or widespread malodors is 2,3 butanedione, discussed above as being incorporated in products of the present invention. In many instances malodorous materials are of basic character. Consequently, it is desirable for the 2,3 butanedione to be incorporated in an acidic complex, preferably having a pH between 0.5 and 1.8.

I claim:

1. A solid deodorant-dispensing product in the form of a floatable solid body of substantial size which is durable and stably form-maintaining when in contact with water, comprising deodorant, release retardant for said deodorant, binder, and floatable material, said binder and floatable material being substantially insoluble in water and substantially nonreactive chemically with water.

2. The product defined in claim 1, including at least one release retardant selected from the group consisting of paradichlorobenzene, paranitrochlorobenzene, dinitrobenzene, dinitrotoluene, dinitronaphthalene, dinitrochlorobenzene and benzophenone.

3. The product defined in claim 1, in which the release retardant includes paradichlorobenzene.

4. The product defined in claim 1, including at least one deodorant selected from the group consisting of musk xylene, vanillin and 2,3 butanedione.

5. The product defined in claim 1, including binder selected from the group consisting of paraffin, gelatin, agar-agar, carrageenin, pectin, cellulose derivative selected from the group consisting of methylcellulose, carboxymethylcellulose, hydroxypropyl methylcellulose and sodium carboxymethylcellulose, and sorbitan derivatives and complexes selected from the group consisting of sorbitan polyoxyethylene monooleate, sorbitan polyoxyethylene monostearate and sorbitan monostearate.

6. The product defined in claim 1, including by weight:

deodorant: 5 to 50 percent
release retardant: 5 to 35 percent
binder: 2 to 40 percent.

7. The product defined in claim 1, in which the deodorant includes 2,3 butanedione.

8. The product defined in claim 1, in which the binder includes paraffin.

9. An extrudable gel adherent to surfaces and solidifiable by brief exposure to air, comprising deodorant, at least one release retardant for said deodorant selected from the group consisting of paradichlorobenzene, paranitrochlorobenzene, dinitrobenzene, dinitrotoluene, dinitronaphthalene, dinitrochlorobenzene and benzophenone, binder for said deodorant and release retardant, and at least one insecticide selected from the group consisting of 2,2-dichlorovinyl dimethyl phosphate, dieldrin, malathion, pyrethrin I and pyrethrin II.

10. An extrudable gel adherent to surfaces and solidifiable by brief exposure to air, comprising deodorant, at least one release retardant for said deodorant selected from the group consisting of paradichlorobenzene, paranitrochlorobenzene, dinitrobenzene, dinitrotoluene, dinitronaphthalene, dinitrochlorobenzene and benzophenone, binder for said deodorant and release retardant, and insect repellent selected from the group consisting of 2-phenylcyclohexanol; 2-ethylhexanediol-1,3; 2-ethyl-2-butylpropanediol-1,3; dimethyl phthalate; and N-butylacetanilide.

11. A solid deodorant-dispensing product which is in the form of a body of substantial size stably form-maintaining when in contact with water and includes by weight
binder: 1 to 50 percent
2,3 butanedione: 0.01 to 10 percent
other deodorant: 1 to 30 percent
release retardant: 1 to 30 percent.

12. A solid deodorant-dispensing product in the form of a floatable, durable, form-maintaining solid body of material including by weight:
binder: 2 to 40 percent
deodorant: 5 to 50 percent
release retardant: 5 to 35 percent
floatable material: 10 to 90 percent,
the binder and floatable material being substantially insoluble in water and substantially nonreactive chemically with water.

13. The product defined in claim 12, in which the deodorant includes 2,3 butanedione.

14. The product defined in claim 12, in which the floatable material includes sawdust.

15. The product defined in claim 12, in which the binder includes principally paraffin and the floatable material includes principally sawdust.

16. A solid deodorant-dispensing product in the form of a floatable solid body stably form-maintaining in contact with water and including at least one biodegradant selected from the group consisting of bacteria, fungi and enzymes.

17. The product defined in claim 16, in which the biodegradant includes a mixed culture of bacteria, fungus and yeast.

18. The product defined in claim 16, including an enzyme biodegradant.

19. The product defined in claim 16, and an adjunct to the floatable body including by weight
floatable material: 0 to 5 percent
inert filler and binder: 5 to 80 percent
mixed culture of bacteria, fungus and yeast: 1 to 50 percent
enzyme degradant: 0 to 50 percent
sugar: 0 to 50 percent.

20. The product defined in claim 16, in which the floatable solid body is a component of annular shape, and, as an adjunct to the floatable solid, a component received within the aperture of the annular component and carrying biodegradant.

21. A deodorant product including a composition of phosphoric acid and biacetyl having deodorant properties, the manifestation of which deodorant properties is prolonged as compared to the duration of the deodorant properties of biacetyl alone.

22. A deodorant floater for lagoons including a floatable body of material the principal portion of which is substantially insoluble in water and substantially nonreactive chemcially with water and carrying a volatilizable deodorant.

23. A lagoon-conditioning floater comprising a floatable body, and biodegradant carried by said body and leachable into the lagoon.

24. The floater defined in claim 23, including vaporizable deodorant carried by the floatable body.

25. A lagoon-conditioning floater comprising a floatable body, volatilizable deodorant carried by said floatable body, and an adjunct to said floatable body carrying biodegradant.

26. The floater defined in claim 25, including at least one biodegradant selected from the group consisting of bacteria, fungi, and enzymes.

27. The method of treating a lagoon which comprises incorporating vaporizable deodorant in a floatable body of substantial size, stably form-maintaining in contact with water, and floating the floatable body on a lagoon for release of vaporizable deodorant from the floatable body to deodorize malodorous gas escaping from the lagoon while the floatable body substantially maintains its integrity over an extended period of time.

28. The method defined in claim 27, including incorporating in the floatable body material releasable for coating the surface of the lagoon.

29. The method defined in claim 27, including incorporating biodegradant in the floatable body for biodegrading organic material in the lagoon.

30. A deodorant-dispensing product comprising deodorant, at least one release retardant selected from the group consisting of paradichlorobenzene, paranitrochlorobenzene, dinitrobenzene, dinitrotoluene, dinitronaphthalene, dinitrochlorobenzene and benzophenone, and binder selected from the group consisting of paraffin, gelatin, agar-agar, pectin, cellulose derivative selected from the group consisting of methylcellulose, carboxymethylcellulose, hydroxypropyl methylcellulose and sodium carboxymethylcellulose, and sorbitan derivatives and complexes selected from the group consisting of sorbitan polyoxyethylene monooleate, sorbitan polyoxyethylene monostearate and sorbitan monostearate.

31. The product defined in claim 30, in which the product is in the form of an extrudable gel adherent to surfaces and solidifiable by brief exposure to air.

32. The product defined in claim 30, in which the product is in the form of a stable form-maintaining solid body of substantial size.

33. The product defined in claim 30, in which the product is in the form of a floatable body of substantial size which is stably form-maintaining in contact with water.

34. The product defined in claim 30, including by weight:
deodorant: 0.1 to 50 percent
release retardant: 1.0 to 80 percent
binder: 1.0 to 70 percent.

35. The method of treating a lagoon which comprises incorporating vaporizable deodorant in a floatable body of material the principal portion of which is substantially insoluble in water and substantially nonreactive chemically with water, and floating the floatable body on a lagoon for release of vaporizable deodorant from the floatable body to deodorize malodorous gas escaping from the lagoon while the floatable body substantially maintains its integrity over an extended period of time.

* * * * *